United States Patent [19]
Augello et al.

[11] Patent Number: 5,955,107
[45] Date of Patent: Sep. 21, 1999

[54] PHARMACEUTICAL SUSPENSION TABLET COMPOSITIONS

[75] Inventors: Michael Augello, Marlboro, N.J.; Sheila M. Dell, New Hope, Pa.; George A. Agyilirah, Plainsboro; George E. Reier, Somerset, both of N.J.

[73] Assignee: FMC Corporation, Philadelphia, Pa.

[21] Appl. No.: 08/989,787

[22] Filed: Dec. 12, 1997

[51] Int. Cl.⁶ .................................................. A61K 9/20
[52] U.S. Cl. ..................... 424/465; 424/441; 424/464; 514/779; 514/781
[58] Field of Search .................... 424/464, 465, 424/441

[56] References Cited

U.S. PATENT DOCUMENTS 4,965,072  10/1990  Alexander et al. ..................... 424/458
5,073,377  12/1991  Alexander et al. ..................... 424/458

FOREIGN PATENT DOCUMENTS

WO 87/05804  10/1987  WIPO .

*Primary Examiner*—James M. Spear
*Attorney, Agent, or Firm*—Ratner & Prestia; Robert L. Andersen; I. Robert Silverman

[57] ABSTRACT

Rapidly disintegrating and readily suspendible tablets and their method of preparation are disclosed in which there is a therapeutic amount of a pharmacologically active ingredient, 1 to 6 percent croscarmellose sodium, 10 to 50 percent microcrystalline cellulose, and 10 to 50 percent of a coprocessed additive consisting essentially of 75 to 95 percent microcrystalline cellulose and 5 to 25 percent calcium, sodium alginate complex. The tablets are suitable for oral administration of measured-dose suspensions of either water soluble or water insoluble pharmaceuticals.

14 Claims, No Drawings

PHARMACEUTICAL SUSPENSION TABLET COMPOSITIONS

The present invention relates to pharmaceutical tablets which disintegrate rapidly in aqueous media and form an aqueous suspension of the active ingredient with minimal shaking or agitation.

The vast majority of pharmaceuticals are administered orally as tablets, capsules and other solid dosage forms. Many patients have trouble swallowing such solid dosage forms, particularly those which are large or capsule shaped. To obviate such problems the pharmaceutical industry has packaged many pharmaceuticals as liquid suspensions, syrups and solutions, which require the patient to measure out individual doses from a larger volume of liquid. Such liquid formulations frequently require refrigeration, are inconvenient to carry when traveling, and entail the possibility of inaccurate measurement and dosing.

Various types of unit dosage forms other than tablets, capsules and the like are also known. For example it is known to create rapidly dissolving powders and granules which are packaged as unit dosages, for example cachets and the like which can be dissolved or suspended in water for ingestion. However, such dosage forms tend to be bulky, the packaging fragile. Spillage and incomplete emptying during opening of packages is not uncommon. Effervescent tablets are also known and commonly used for dissolving antacids and cold and cough remedies in water for administration, but such tablets tend to be large, relatively slow to dissolve, and have not had wide spread acceptance for other active ingredients.

Accordingly, there is a continuing need in the industry for tablets which will accurately deliver precise dosages of pharmacologically active ingredients, which dissolve rapidly when placed in water, and which form suspensions of the active ingredient with minimal shaking, stirring or other agitation.

The present invention provides pharmaceutical suspension tablets which utilize commonly available materials and achieve these and other desirable objectives. The tablets of this invention provide for precise dosing of a wide range of active agents which may be either soluble or insoluble in water. They are particularly usefull for medicating children and the elderly and others in a way that is much more acceptable than swallowing or chewing a tablet. The tablets that are produced have low friability, making them easily transportable. They avoid the need and nuisance and commercial expense of transporting water and minimize the possibility for errors in dosing. While the pharmaceutical tablets of this invention are primarily intended as a suspension dosage form, the granulations used to form the tablet may be used to form rapidly disintegrating chewable tablets, lozenges, or swallowable tablets, as well as suspension tablets. Thus, the intermediate formulations as well as the process for preparing them provide additional novel aspects of the present invention.

The pharmaceutical suspension tablets of this invention comprise, in combination, a therapeutic amount of a pharmacologically active ingredient, croscarmellose sodium, microcrystalline cellulose, and a coprocessed additive containing microcrystalline cellulose and a calcium, sodium alginate complex. More particularly the pharmaceutical suspension tablets comprise a therapeutic amount of a pharmacologically active ingredient, 1 to 6 percent croscarmellose sodium, 10 to 50 percent microcrystalline cellulose, and 10 to 50 percent of a coprocessed additive consisting essentially of 75 to 95 percent microcrystalline cellulose and 5 to 25 percent of a calcium, sodium alginate complex.

As used herein the term 'pharmaceutical suspension tablets' refers to compressed tablets which disintegrate within a few seconds after they are placed in water and are readily dispersible to form a suspension containing a precise dosage of the pharmacologically active ingredient. Unless expressly indicated otherwise, all percentages are by weight.

In the formulation of this invention the pharmaceutically active ingredient must be present in a therapeutically effective amount. That amount, however, may vary widely from formulation to formulation and from ingredient to ingredient. In general however, the pharmacologically active ingredient will be utilized at a level in the range of about 0.25% to about 65% of the finished tablet formulation, although a level in the range of about 15% to about 60 percent is more typical.

Croscarmellose sodium is a known disintegrant for tablet formulations, and is available from FMC Corporation, Philadelphia, Pa. under the trademark Ac-Di-Sol®. It is frequently blended in compressed tableting formulations either alone or in combination with microcrystalline cellulose to achieve rapid disintegration of the tablet. In the present invention, however, it is used in an aqueous slurry which coats the active ingredient during granulation. Depending on the particular formulation it may be utilized in an amount which is about 1% to about 6% of the tablet formulation, preferably in the range of about 2% to about 4%.

Microcrystalline cellulose, alone or coprocessed with other ingredients, is also a common additive for compressed tablets and is well known for its ability to improve compressibility of difficult to tablet materials. It is commercially available under the Avicel® trademark. In the present formulations, two different Avicel® products are utilized, Avicel® PH which is microcrystalline cellulose per se, and Avicel® AC-815, a coprocessed spray dried residue of microcrystalline cellulose and a calcium, sodium alginate complex in which the calcium to sodium ratio is in the range of 0.43: 1 to 2.33: 1. While AC-815 is comprised of 85% microcrystalline cellulose (MCC) and 15% of a calcium, sodium alginate complex, for purposes of the present invention this ratio may be varied from about 75% MCC to 25% alginate up to about 95% MCC to 5% alginate. Depending on the particular formulation and active ingredient, these two components may be present in approximately equal amounts or in unequal amounts, and either may comprise from about 10% to about 50% by weight of the tablet.

The tablet composition may, in addition to the ingredients described above, contain other ingredients often used in pharmaceutical tablets, including flavoring agents, sweetening agents, flow aids, lubricants or other common tablet adjuvants, as will be apparent to those skilled in the art.

While the specific combination of ingredients of the tablets forms an important aspect of the present invention, the process by which they are made is also an important aspect.

In general the tablets are prepared from a granulation of croscarmellose sodium and the pharmacologically active ingredient, and optionally, depending largely on the solubility of the active ingredient, microcrystalline cellulose. The granulations are prepared by making a slurry of croscarmellose sodium in a limited amount of water and then utilizing this slurry as the source of water to granulate an active agent. By this method, the active agent, if it has a low solubility in water, is effectively coated with the croscarmellose sodium, enabling the disintegrant to act unusually rapidly when the granulation is incorporated into a tablet composition. If the active agent is water soluble, then microcrystalline cellulose is added to the granulation to absorb the active agent and in turn be coated with the croscarmellose sodium. The granulations are then dried.

The dried granulations may then be formulated in the dry state with Avicel® AC-815 (microcrystalline cellulose coprocessed with a calcium, sodium alginate complex, 85:15), a PH grade of Avicel® microcrystalline cellulose, and with other conventional tablet additives, for example a lubricant such as magnesium stearate, natural or synthetic sweeteners, flow aids and the like. This composition may then be compressed into tablets which, when put in a small amount of water, dissolve within 10–30 seconds, forming a suspension with minimal shaking or agitation.

Thus, the process for preparing the rapidly disintegrating tablets of the instant invention comprises the following steps:

(a) preparing a slurry of croscarmellose sodium in water;

(b) granulating together the croscarmellose sodium slurry and a granulation substrate comprising a pharmacologically active agent, said slurry being used as the source of water for the granulation;

(c) drying the granulation product of step (b);

(d) blending together the dried granulation from step (c), microcrystalline cellulose, and a coprocessed additive consisting essentially of 75 to 95 percent microcrystalline cellulose and 5 to 25 percent of a calcium, sodium alginate complex, and optional additives selected from lubricants, sweetening agents, and flavoring agents and mixtures thereof, to form a dry tableting composition; and (e) forming the tableting composition into said pharmaceutical suspension tablets.

In step (a) of the process, croscarmellose sodium is preferably employed in an amount which is in the range of about, 2% to about 15% of the amount of pharmacologically active ingredient to be utilized in step (b), advantageously about 5% to about 12%. In step (a) it is important to limit the amount of water in which the croscarmellose sodium is slurried to just that which is required to granulate the granulation substrate of step (b). Also, because the croscarmellose sodium has significant solubility in water, the time from its introduction into the water until the actual granulation is begun must likewise be limited. This appears to enhance the coating of the active agent with the croscarmellose sodium.

The effect of croscarmellose sodium on the final product formed in the process is quite surprising since it is a member of a group of disintegrants characterized as "super disintegrants", which includes crospovidone and sodium starch glycolate. Both of these disintegrants have been tried in this granulating system, and both failed to provide the desired results. The sodium starch glycolate developed a ropy consistency in the slurry which inhibited its effectiveness. The crospovidone did not provide adequate coverage to effect the desired rapid disintegration.

The precise mix of ingredients utilized in step (b) will vary with each pharmaceutically active ingredient and its properties. In granulating a relatively water insoluble active it is generally not necessary to include microcrystalline cellulose in the granulation substrate. However, in granulating a water-soluble active agent, microcrystalline cellulose is included in the granulation substrate. The amount of microcrystalline cellulose to be included in the granulation substrate is about 70% to about 115% by weight of the active being granulated, preferably about 85% to about 110% by weight.

As indicated earlier, the amount of granulated active agent which can be formulated in the tablet composition also ranges widely from about 0.25% to about 60% by weight of the entire composition, preferably 15% to 60% by weight.

In Step (c), the manner or drying is not considered critical to the success of the process. Thus, the granulation may be dried in an oven, air dried, or dried in any other convenient manner.

In Step (d) both microcrystalline cellulose (MCC) and the coprocessed additive described above (including Avicel® AC-815 or variants of it), are necessary ingredients in the process. It has been found that this unique combination of ingredients contributes to the compressibility of the composition and facilitates the suspendibility in a small amount of water upon tablet disintegration. Both excipients may be present in either equal or unequal amounts. The amounts of each of these excipients employed in step (d) range from about 10% to about 50% by weight of the entire composition, preferably 15% to 35% by weight.

A wide range of active agents may be formulated according to the method of this invention. These include: analgesics, antipyretics, antibiotics, cough and cold drugs, antiepileptics, antihistamines, cardiovascular drugs, gastrointestinal drugs, respiratory drugs, vitamins, and combinations of two or more of these classes of drugs. The active agents can be either relatively insoluble in water or quite soluble; however, the latter require the addition of microcrystalline cellulose in the granulation step.

The following examples are illustrative of the processes used to prepare granulations of water-insoluble and water-soluble active agents. It should be noted that disintegration times in both examples are similar regardless of the hardness of the tablets. Furthermore, the friability is very low, even when the hardness of the tablets is extremely low. A unique property of these tablets is the combination of rapid disintegration and the ability to form a suspension easily after disintegration has occurred.

EXAMPLE 1

Fast Disintegrating Tablets of Acetaminophen

To the vortex of a rapidly stirred large beaker containing 2.85 kilograms of deionized water was added 300 grams of croscarmellose sodium, forming a slurry. This slurry was mixed for 10 minutes. Concurrently, 5.0 kilograms of powdered acetaminophen was placed in the bowl of a Hobart mixer. At the conclusion of the mixing time for the slurry of croscarmellose sodium, the slurry was added slowly to the acetaminophen in the mixer bowl, forming a granulation which was then placed in trays and dried in a 70° C. oven for three hours. The dry granulation was then passed through a US Standard 14 mesh screen (1410 microns). Dry granulation (4796 grams) was then placed in a twin shell blender, and to it were added 1584 grams of Avicel® AC-815 (85% microcrystalline cellulose coprocessed with 15% of a calcium, sodium alginate complex and 1584 grams of microcrystalline cellulose (Avicel® PH-302). This was thoroughly blended for 10–15 minutes after which 36.24 grams of magnesium stearate was added and mixed for an additional 5 minutes. Prior to being added to the blender the magnesium stearate had been passed through a US Standard 30 mesh screen. The resulting blend was compressed into caplet-shaped tablets on a Hata Tablet Press HS. These tablets had an average weight of 0.884 grams and an average thickness of 7.869 mm (0.3098 inch). The hardness of these tablets averaged 11.98 Kiloponds. Friability of these tablets was measured at 0.433% after 10 minutes and 0.847% after 19 minutes. The average disintegration time was 26 seconds in 10 ml of deionized water, forming a suspension with minimal shaking.

EXAMPLE 2

Fast Disintegrating Tablets of Pseudoephedrine Hydrochloride

To the vortex of a rapidly stirred beaker containing 345 grams of deionized water was added 30 grams of croscarmellose sodium. This slurry was mixed for 10 minutes. Concurrently, 300 grams of pseudoephedrine hydrochloride and 300 grams of microcrystalline cellulose (Avicel® PH-101), were placed in the bowl of a Hobart mixer. This mixture was stirred for 10 minutes. At the conclusion of the mixing time, the slurry was added slowly to the contents of the mixing bowl, forming a granulation which was then placed in trays and dried in a 65° C. oven for three hours. The dried granulation was passed through a US Standard 16 mesh screen (1190 microns). The dried granulation was then placed in a twin shell blender, and to it were added 300 grams of Avicel® AC-815 (85% microcrystalline cellulose coprocessed with 15% of a calcium, sodium alginate complex) and 300 grams of microcrystalline cellulose (Avicel® PH-102). This was thoroughly blended for 10 minutes, after which 10.05 grams of magnesium stearate was added and mixed for an additional 5 minutes. Prior to being added to the blender the magnesium stearate had been passed through a US Standard 30 mesh screen. The resulting blend was compressed into tablets on a B2 Tablet Press using 6.35 mm (0.25 inch) round standard concave tooling. These tablets had an average weight of 0.1299 grams and an average thickness of 4.864 mm (0.1915 inch). The hardness of these tablets averaged 1.38 Kiloponds. Friability was measured at 0.077% after 4 minutes. The average disintegration time was 15 seconds in 10 ml of deionized water, forming a suspension with minimal shaking.

We claim:

1. A pharmaceutical suspension tablet comprising a therapeutic amount of a pharmacologically active ingredient selected from the group consisting of analgesics, antipyretics, antibiotics, cough and cold drugs, antiepileptics, antihistamines, cardiovascular drugs, gastrointestinal drugs, respiratory drugs, vitamins, and combinations of two or more of these classes of drugs, 1 to 6 percent croscarmellose sodium, 10 to 50 percent microcrystalline cellulose, and 10 to 50 percent of a coprocessed additive consisting essentially of 75 to 95 percent microcrystalline cellulose and 5 to 25 percent of a calcium, sodium alginate complex.

2. Pharmaceutical suspension tablets of claim 1 which comprise 0.25 to 60 percent of said pharmacologically active ingredient.

3. The pharmaceutical suspension tablets of claim 1 in which said pharmacologically active ingredient is insoluble or only slightly soluble in aqueous media.

4. The pharmaceutical suspension tablets of claim 1 in which the pharmacologically active ingredient is acetaminophen, or pseudoephedrine hydrochloride.

5. The pharmaceutical suspension tablets of claim 1, said tablets including additional components comprising compatible pharmaceutically acceptable additives selected from the group consisting of lubricants, sweetening agents, flavoring agents, and mixtures thereof.

6. The pharmaceutical tablets of claim 1 which are pharmaceutical suspension tablets for administration by disintegrating and suspending the tablet ingredients in a small amount of water.

7. The pharmaceutical tablets of claim 1 comprising a lozenge, chewable tablet or swallowable tablet.

8. A method for manufacture of pharmaceutical suspension tablets comprising the steps:

(a) preparing a slurry of croscarmellose sodium in water;

(b) granulating together the croscarmellose sodium slurry and a granulation substrate comprising a pharmacologically active agent, said slurry being used as the source of water for the granulation;

(c) drying the granulation product of step (b);

(d) blending together the dried granulation from step (c), microcrystalline cellulose, and a coprocessed additive consisting essentially of 75 to 95 percent microcrystalline cellulose and 5 to 25 percent of a calcium, sodium alginate complex, and optional additives selected from the group consisting of lubricants, sweetening agents, flavoring agents and mixtures thereof, then (e) forming the tableting composition into said pharmaceutical suspension tablets, said tablets comprising a therapeutic amount of a pharmacologically active ingredient selected from the group consisting of analgesics, antipyretics, antibiotics, cough and cold drugs, antiepileptics, antihistamines, cardiovascular drugs, gastrointestinal drugs, respiratory drugs, vitamins, and combinations of two or more of these classes of drugs, 1 to 6 percent croscarmellose sodium, 10 to 50 percent microcrystalline cellulose, and 10 to 50 percent of said coprocessed additive.

9. The method of claim 8 in which said pharmacologically active agent is insoluble or slightly soluble in aqueous media and the granulation substrate consists essentially of said active agent.

10. The method of claim 8 in which the pharmacologically active agent is moderately to highly soluble in aqueous media and the granular substrate consists essentially of the active agent and from 70% to about 115% microcrystalline cellulose, based on the amount of active agent employed in the granulation substrate.

11. The process of claim 8 in which the granulation substrate also includes compatible pharmaceutically acceptable additives selected from the group consisting of lubricants, sweetening agents, flavoring agents, and mixtures thereof.

12. A formulation for preparation of rapidly dissolving pharmaceutical dosage forms comprising from 0.25 to 60 percent pharmacologically active ingredient selected from the group consisting of analgesics, antipyretics, antibiotics, cough and cold drugs, antiepileptics, antihistamines, cardiovascular drugs, gastrointestinal drugs, respiratory drugs, vitamins, and combinations of two or more of these classes of drugs, 1 to 6 percent croscarmellose sodium, 10 to 50 percent microcrystalline cellulose, and 10 to 50 percent of a coprocessed additive consisting essentially of 75 to 95 percent microcrystalline cellulose and 5 to 25 percent of a calcium, sodium alginate complex.

13. The formulation of claim 12 in which the active ingredient is employed at a level in the range of 15% to 60% of said formulation.

14. The formulation of claim 11 or 12 which includes compatible pharmaceutically acceptable additives selected from the group consisting of lubricants, sweetening agents, flavoring agents, and mixtures thereof.

* * * * *